United States Patent [19]
Habif et al.

[11] Patent Number: 5,744,148
[45] Date of Patent: Apr. 28, 1998

[54] STABILIZATION OF AN UNSTABLE RETINOID IN OIL-IN-WATER EMULSIONS FOR SKIN CARE COMPOSITIONS

[75] Inventors: Stephan Samuel Habif, Demarest, N.J.; Alexander Lips, London, England; Prem Chandar, Closter; Mark Edward Rerek, Scotch Plains, both of N.J.

[73] Assignee: Chesebrough-Pond's USA Co., Division of Conopco, Inc., Greenwich, Conn.

[21] Appl. No.: 717,046

[22] Filed: Sep. 20, 1996

[51] Int. Cl.$^6$ ................................................. A61K 7/48
[52] U.S. Cl. ........................... 424/401; 514/725; 514/937
[58] Field of Search ............................. 424/401, 725; 514/937

[56] References Cited

U.S. PATENT DOCUMENTS

| | | | |
|---|---|---|---|
| 3,906,108 | 9/1975 | Felty | 424/318 |
| 4,333,924 | 6/1982 | Bowley et al. | 424/170 |
| 4,826,828 | 5/1989 | Wilmott et al. | 514/63 |
| 4,888,363 | 12/1989 | Dulak et al. | 514/725 |
| 4,981,845 | 1/1991 | Pereira | 514/557 |
| 5,037,850 | 8/1991 | Elliott et al. | 514/529 |
| 5,380,764 | 1/1995 | Herzog | 514/725 |
| 5,484,816 | 1/1996 | Yanagida et al. | 514/725 |
| 5,492,894 | 2/1996 | Bascom et al. | 514/18 |

FOREIGN PATENT DOCUMENTS

| | | |
|---|---|---|
| 0 440 398 | 8/1991 | European Pat. Off. . |
| 0 631 772 | 1/1995 | European Pat. Off. . |
| 93/00085 | 1/1993 | WIPO . |
| WO 93/19743 | 10/1993 | WIPO . |

OTHER PUBLICATIONS

Idson, "Vitamins and the Skin", Cosmetics & Toiletries, vol. 108, Dec. 1993, pp. 79–94, Allured Publishing Corp. (1993).
Hoffman–La Roche Inc., Data Sheet "Vitamin A–The 'Normalizer'", Roche Vitamins & Fine Chemicals.
Hoffman–La Roche, Inc., Product Data "Vitamin A Alcohol Blend", Roche Vitamins & Fine Chemicals.
Chemical Abstract No. 108:226682j of RO92,576 published Oct. 30, 1987.
Chemical Abstract No. 109:61310s of RO 93,807 published Feb. 29, 1988.
Chemical Abstract No. 102:209427p of RO 84,823 published Sep. 30, 1984.
Chemical Abstract No. 97:78681v of JP 82 70 808 published May 1, 1982.
Translation of Claims of Canadian Patent Application 2,138,112.
Ingredients Label for Pond's® Age Defying Complex, Dec. 1, 1993.

*Primary Examiner*—Jyothsna Venkat
*Attorney, Agent, or Firm*—Rimma Mitelman

[57] ABSTRACT

Oil-in-water emulsions containing an unstable retinoid (retinol or $C_2$–$C_3$ ester thereof) in an oil phase. The retinoid is stabilized in the inventive emulsions, despite the presence of from about 50% to about 98% of an aqueous phase. The emulsions also preferably include a hydroxy acid.

8 Claims, No Drawings

STABILIZATION OF AN UNSTABLE RETINOID IN OIL-IN-WATER EMULSIONS FOR SKIN CARE COMPOSITIONS

FIELD OF THE INVENTION

Skin care compositions containing retinol or short chain esters thereof in an oil-in-water emulsion.

BACKGROUND OF THE INVENTION

Natural and synthetic vitamin A derivatives have been used extensively in the treatment of a variety of skin disorders and have been used as skin repair or renewal agents. Retinoic acid has been employed to treat a variety of skin conditions, e.g., acne, wrinkles, psoriasis, age spots and discoloration. See e.g., Vahlquist, A. et al., *J. Invest. Dermatol.*, Vol. 94, Holland D. B. and Cunliffe, W. J. (1990), pp. 496–498; Ellis, C. N. et al., "Pharmacology of Retinols in Skin", Vasel, Karger, Vol. 3, (1989), pp. 249–252; Lowe, N. J. et al., "Pharmacology of Retinols in Skin", Vol. 3, (1989), pp. 240–248; PCT Patent Application No. WO 93/19743.

It is believed that the use of retinol or short chain esters of retinol would be preferred over retinoic acid. Retinol is an endogenous compound which occurs naturally in the human body and is essential for normal epithelial cell differentiation. Short chain esters of retinol hydrolyze in-vivo to produce retinol. Retinol and retinyl esters are considered to be safer than retinoic acid.

Long chain retinyl esters, especially retinyl palmitate, have been used extensively in skin cosmetic compositions. Such compositions may be oil-in-water emulsions, as for instance Age Defying Complex® produced by Chesebrough-Pond's. However, it has been found as part of the present invention that retinol or short chain esters of retinol are more efficacious than long chain esters of retinol, such as retinyl palmitate (see Example 7). It is believed that retinyl palmitate does not hydrolyze in-vivo to produce retinol and/or does not penetrate skin.

Unfortunately, retinol and short-chain retinyl esters are more unstable than retinoic acid or long chain retinyl esters, See Idson, "Vitamins and the Skin", Cosmetics & Toiletties, Vol. 108, December 1993, pp. 79–94, Allured Publishing Corp. (1993); Hoffman-La Roche Inc., Data Sheet "Vitamin A—The 'Normalizer'", Roche Vitamins & Fine Chemicals; Hoffman-La Roche Inc., Product Data "Vitamin A Alcohol Blend". Specifically, they rapidly degrade in the presence of water.

Anhydrous retinol-containing compositions are known in the art. See for instance Dulak et al., U.S. Pat. No. 4,888,363 and Wilmott et al., U.S. Pat. No. 4,826,828. But such compositions do not generally include water-soluble skin benefit ingredients, especially if such ingredients are to be included in high amounts.

Water-in-oil emulsions which contain retinol in an oil phase are also known. See for instance European Patent 440,398 (Johnson and Johnson), International patent application WO 93/0085 (Johnson & Johnson), and European Patent application 631,772 (Johnson & Johnson). A serious drawback of both anhydrous compositions and water-in-oil emulsions is that they are greasier and cosmetically less appealing than oil-in-water emulsions because the continuous phase is an oil phase. See page 2, lines 13–16, of EP '492.

Thus, it is desirable to formulate retinol or short-chain esters of retinol into oil-in-water emulsions. However, due to a greater exposure of a retinoid to aqueous phase in such systems (compared to anhydrous systems or water-in-oil emulsions), it has not been possible to stabilize an unstable retinoid in such systems. See for instance the above cited European Patent 440,398 which teaches at page 1, lines 34–37, that retinoids in oil-in-water emulsions "are unstable . . . and chemically degrade and are, therefore, unavailable over time for their alleged utility." The above-cited International application WO 930085 teaches at page 8, lines 2–7: "For reasons which are not clearly understood, stability satisfactory for a commercial product has been achievable for certain specific retinoids only by utilizing a specific form of emulsion, i.e. water-in-oil, and then, only by employing a specific stabilizing system."

The present invention is based, in part, on the discovery that an unstable retinoid, i.e. retinol or short chain esters thereof, may be stabilized in oil-in-water emulsions by virtue of combination of several critical parameters, such as: employing a specific oil phase to form oil droplets containing a solubilized unstable retinoid and employing selected combinations of solid compounds to form a barrier layer of specifically sized crystals for the oil droplets.

The solid compounds and/or the oils employed in the present invention for forming oil droplets surrounded by a crystalline barrier layer have been used in skin care compositions, e.g. as emollients. Some of these compositions also include retinoids, most often retinoic acid or retinyl palmitate. See for instance abstract of Romanian patents RO 92,576, RO 93,807, RO 84,823; U.S. Pat. No. 3,906,108 (Felty et al.); U.S. Pat. No. 5,380,764 (Herzog); U.S. Pat. No. 4,981,845 (Pareira et al.); U.S. Pat. No. 5,037,850 (Elliott et al.); U.S. Pat. No. 4,333,924 (Bowlay et al.); U.S. Pat. No. 5,492,894 (Bascom et al.). However, such compositions differ from the present invention in at least that they do not contain an unstable retinoid (retinol or short chain esters thereof) within oil droplets surrounded by a barrier of defined size crystals. The prior art does not provide a stable oil-in-water emulsion containing retinol or short-chain esters thereof.

SUMMARY OF THE INVENTION

The present invention includes, in part, an oil-in-water emulsion for skin conditioning, the emulsion comprising:
(a) an oil phase comprising from about 0.1% to about 50%, by weight of the emulsion, of oil droplets comprising a fluid oil and from about 0.001 to about 10%, by weight of the emulsion, of a retinoid selected from the group consisting of retinol and $C_2$–$C_3$ esters of retinol, wherein the retinoid is solubilized in the oil;
(b) from about 50% to about 98%, by weight of the emulsion, of an aqueous phase; and
(c) from about 1% to about 20% by weight of the emulsion of a barrier ingredient, wherein the barrier ingredient provides a crystalline barrier layer between the oil droplets and the aqueous phase, wherein the size of the crystals in the barrier layer, as determined by a Microscopic Crystal Sizing Test (described hereinbelow), is in the range of from about 1 μm to about 50 μm;

and wherein the size ratio of an individual oil droplet to an individual crystal in the barrier layer is in the range of from about 5:1 to about 100:1;

and wherein the melting point of a mixture of the fluid oil and the barrier ingredient is in the range of from about 40° C. to about 100° C.

The term "conditioning" as used herein means prevention and treatment of dry skin, photodamaged skin, appearance of wrinkles, age spots, aged skin, increasing stratum corneum flexibility, and generally increasing the glow, radiance, and quality of skin. The composition may be used to improve skin desquamation and epidermal differentiation.

According to the present invention, by virtue of creating oil droplets containing a solubilized unstable retinoid and surrounded by a barrier of crystals of a defined size range, the stability of the retinoid in an oil-in-water emulsion is substantially improved. The presence of oil droplets containing the retinoid and surrounded by the crystalline barrier is ensured according to the present invention by selecting fluid oils and barrier ingredients which satisfy the melting point, crystal size and solubility requirements described in a greater detail hereinbelow.

DETAILED DESCRIPTION OF THE INVENTION

The oil-in-water emulsion included in the inventive compositions contains oil droplets in a continuous aqueous phase.

The oil droplets contain, as a first essential ingredient, a retinoid selected from the group consisting of retinol and $C_2$-$C_3$ esters of retinol. As illustrated in Example 7, these compounds are more efficacious than retinyl palmitate.

The term "retinol" as used herein includes the following isomers of retinol: all-trans-retinol, 13-cis-retinol, 11-cis-retinol, 9-cis-retinol, 3,4-didehydro-retinol. Preferred isomers are all-trans-retinol, 13-cis-retinol, 3,4-didehydro-retinol, 9-cis-retinol. Most preferred is all-trans-retinol, due to its wide commercial availability.

Retinyl ester is an ester of retinol. The term "retinol" has been defined above. Retinyl esters suitable for use in the present invention are $C_2$ and $C_3$ esters of retinol, also known as retinyl acetate and retinyl propionate. Retinyl acetate is an especially preferred ester because it is the most efficacious, the most commercially available and the cheapest. For the same reasons, the most preferred retinoid for use in the present invention is retinol.

Retinol or a retinyl ester is employed in the inventive composition in an amount of from about 0.001% to about 10%, by weight of the emulsion, preferably in an amount of from about 0.01% to about 0.5%, most preferably in an amount of from about 0.05% to about 0.2%.

The second essential ingredient of the oil phase in the inventive emulsions is a fluid oil. The oil phase in the inventive emulsions may be formed of a single compound or a mixture of compounds. The oil phase according to the present invention must be fluid and must be capable of solubilizing, at a storage temperature (typically 25° C.), the required amount of retinol or $C_{2-3}$ esters thereof. Furthermore, a mixture of the oil phase and the barrier ingredient must satisfy the melting point test discussed in more detail below. The term "fluid" as used herein means that at least 50% of an oil is liquid at 25° C.

Suitable compounds to form the oil phase include but are not limited to esters of fatty acids or alcohols and hydrocarbons, preferably monoesters of fatty acids or alcohols, as long as they satisfy the melting point and solubility requirements described herein. Most preferably, fluid oil is selected from the group consisting of isostearyl palmitate, tridecyl salicylate, $C_{12-15}$ octanoate, isopropyl stearate, isopropyl myristate and isopropyl palmitate.

The oil droplets containing the retinoid may be included in the present emulsions in an amount of from about 0.1% to about 50% by weight of the emulsion, preferably from about 1% to about 30%, most preferably from about 5% to about 15%.

The third essential component of the inventive emulsions is a barrier ingredient. The term "barrier ingredient" as used herein means a mixture of at least two compounds: the first compound is a compound employed for the formation of crystals ("crystal-forming compound"); the second compound is the compound required to control the size of the crystals ("crystal-sizing compound"). It was found, as part of the present invention, that if only a crystal-forming compound is employed, the crystals formed are too large (see Example 4) and the retinoid is unstable in such compositions. It was also found that the second, crystal-sizing compound, although unable to form crystals of sufficient size on its own, controls the size of the crystals (see Example 5). The co-presence of the crystal-sizing compound is necessary to stabilize the retinoid.

The size of the crystals is critical to ensure the stability of the inventive emulsions. If the crystals surrounding the oil droplet are too large, the crystals will migrate away from the oil/water interface and remain as separate entities in the emulsion. If the crystals are too small, the exposure of oil phase to water is increased. In both cases, the stability of a retinoid in an oil phase is impaired. The average size of an individual crystal in the inventive emulsions, as determined by the Microscopic Crystal Sizing Test, is in the range of from about 1 to about 50 microns, preferably in the range of from about 1 to about 20 microns and most preferably in the range of from about 5 to about 10 microns. The identity and the amounts of the ingredients that make up the fluid phase and the crystalline barrier determine the size of the crystals.

Microscopic Crystal Sizing Test

The intended fluid oil and barrier forming compounds are co-melted in the same proportions as those intended for the final emulsion. A drop of the co-melt mixture is placed on a microscope slide with a cover slip. Observe in the microscope the size and shape of the crystals. Crystals should be small and relatively smooth (not like sharp needles). The size is determined by taking a micrograph and measuring crystals with a ruler, taking into account the magnification. Several crystals (i.e. at least 5 crystals, and preferably at least 10 crystals) must be sized and averaged, to prevent the risk of measuring an atypical crystal or a cluster of crystals.

Initially, the crystallization pattern may be qualitatively observed using light microscopy under crosspolar conditions. If the initial observation is that the crystals may be of a suitable size, the Microscopic Crystal Sizing Test, as described above, is conducted.

Melting Point

Furthermore, the barrier ingredient and the fluid oil must be so selected, and in such amounts, that the melting point of the mixture is in the range of from about 40° C. to about 100° C. The melting point must be in this range in order to ensure that the crystalline barrier is present during storage, yet the oil phase is released during the topical application. Preferably, the melting point of the mixture is in the range of from about 40° C. to about 75° C., most preferably in the range of from about 45° C. to about 55° C. Furthermore, the melting point of the mixture of the fluid oil and the barrier ingredient components must be quite sharp, i.e. the components in the barrier ingredient and the fluid oil must all be very compatible with each other. The spread in the melting point must be no greater than 25° C., preferably no greater than 10° C., most preferably the melting point is a single sharp peak as determined by Differential Scanning Calorimetry(DSC).

The barrier ingredient (i.e. the mixture of the at least two classes of components that form the barrier layer) is employed in the inventive compositions in an amount of from about 1% to about 20% by weight of the emulsion, preferably in the amount of from about 5% to about 15%, most preferably in an amount of from about 8% to about 12%.

As explained above, the barrier layer according to the present invention is formed by the interaction of at least two components: the crystal-forming component and the crystal-sizing component. The crystal-sizing component is added at levels of from about 1% to about 75%, by weight of the crystal-forming component, preferably from about 5% to about 40%, most preferably from about 10% to about 20%.

Suitable crystal-forming compounds for use in the inventive emulsions include but are not limited to fatty acids, mixtures of fatty acids with their soaps, fatty alcohols and ethoxylated derivatives of fatty acids or fatty alcohols, and sterols (e.g. lanolin or cholesterol). Preferably, the crystal-forming compounds are selected from the group consisting of $C_{12}$–$C_{22}$ (preferably, $C_{16}$–$C_{22}$) fatty acids or alcohols or ethoxylated derivatives thereof, and mixtures thereof. Most preferably, the crystal-forming compounds are selected from the group consisting of palmitic acid, stearic acid, stearyl alcohol, cetyl alcohol, behenic acid, behenyl alcohol, cholesterol and sorbitan stearate, and mixtures thereof.

The crystal-sizing component of the barrier ingredient is selected from the group consisting of hydroxylated fatty acids or alcohols ($C_{12}$–$C_{22}$), and ethoxylated derivatives thereof. Preferably, hydroxylated fatty acids or alcohols or mixtures are employed. The preferred chain length is $C_{16}$–$C_{22}$. Most preferably, the crystal size-controlling component is selected from the group consisting of glyceryl monohydroxystearate, hydroxystearic acid, isostearyl alcohol, isostearic acid.

The crystal-sizing component may or may not be contained in the actual crystals forming a crystalline barrier layer. The crystal-sizing component regulates the size of the crystal and thus is essential in forming a suitable crystal barrier, but its location may be in the crystal or may be in the oil droplet or a combination of the two locations.

The relative size of the individual oil droplet to the individual crystal in the inventive emulsions is in the range of from about 5:1 to about 100:1, preferably in the range of from about 5:1 to about 50:1, most preferably is in the range of from about 5:1 to about 20:1. The crystal size is measured by Microscopic Crystal Sizing Test as described above. The oil droplet size may also be measured by Microscopic Crystal Sizing Test or by using a particle size analyzer (e.g., Mastersizer®).

The overall size of a particle formed of an oil droplet and crystals surrounding the droplet is also important according to the present invention. The half-life of the retinoid in the particle is inversely related to the size of the particle. The larger the particle, the slower is diffusion of the retinoid. Yet the physical stability of the emulsion is affected if the particle size is too large. Thus, the particle size must be such as to attain the chemical stability of the retinoid, yet to preserve the physical stability of the emulsion. It has been found as part of the present invention that the average particle size volume-weighted should be in the range of from about 5 microns to 500 microns, preferably in the range of from about 10 to 50 microns.

This particle size may be measured by using Particle Size Analyzer (e.g. Mastersizer®) and measuring d(5,3) or d(4,3) average particle diameter, as described in Mastersizer manual.

Another essential ingredient of the inventive compositions is in aqueous phase. The aqueous phase of the inventive compositions comprises at least 20% water. However, a particular advantage of the inventive compositions is that they may incorporate a large of amount of an aqueous phase. The preferred compositions contain at least 40% water, preferably from 40% to 95% water, most preferably from 60% to 70% water. An aqueous phase may optionally contain other water soluble solvents or ingredients. Particularly preferred water soluble ingredient incorporated in a aqueous phase is a hydroxy acid as described in greater detail hereinbelow. The total aqueous phase is preferably at least 65%, most preferably at least 70%, by weight of the composition.

The inventive compositions have a half-lifetime of at least 15 days at 50° C., preferably from 20 days to 45 days, most preferably from 35 to 45 days.

"Half-lifetime" is defined as the time it takes for retinol or short-chain ester thereof to degrade to half of its original concentration at a given temperature.

The preferred compositions according to the invention are essentially free of lower chain simple alcohol, such as methanol, ethanol, or propanol, to avoid the drying and irritating effect of such alcohols on the skin.

pH of the compositions is in the range of from 2.5 to 10. Preferred inventive compositions have a pH of from about 6 to about 9, most preferably from about 6.5 to about 7.5.

It should be understood that the inventive emulsions may be co-mixed with other emulsions, including multiple emulsions. Furthermore, the inventive emulsions may contain other oil droplets which may not contain a fluid oil or the retinoid of the invention. A composition is within the scope of the invention as long as it contains an oil-in-water emulsion, the oil phase of which contains from about 0.1% to about 50% of oil droplets described herein.

Optional Skin Benefit Materials and Cosmetic Adjuncts

Various types of skin benefit ingredients may be present in cosmetic emulsions of the present invention. Although not limited to this category, general examples include anti-wrinkle compounds and sunscreens and tanning agents.

A particularly preferred optional ingredient is a hydroxyacid. One of the advantages of the inventive emulsions is that they can incorporate a high amount of the aqueous phase. Consequently, a high amount of water-soluble actives in general and hydroxyacids in particular can be co-present with a retinoid active.

The hydroxy acid can be chosen from α-hydroxy acids, β-hydroxyacids, other hydroxycarbolic acids (e.g., dihydroxycarboxylic acid, hydroxydicarboxylic, hydroxytricarboxylic) and mixtures thereof or combination of their stereoisomers (DL, D or L).

Preferably the hydroxy acid is chosen from α-hydroxy acids having the general structure (13):

where M is H— or $CH_3(C_fH_g)_h$—, f is an integer of from 1 to 27, g is an integer of from 2 to 54, and h is 0 or 1.

Even more preferably the hydroxy acid is chosen from glycolic acid, lactic acid, 2-hydroxyoctanoic acid, hydroxylauric acid and mixtures thereof. When stereo isomers exist, L-isomer is most preferred.

Preferably the amount of the hydroxy acid component present in the emulsion according to the invention is from 0.01 to 20%, more preferably from 0.05 to 12% and most preferably from 0.5 to 8%, by weight of the emulsion.

Sunscreens include those materials commonly employed to block ultraviolet light. Illustrative compounds are the derivatives of PABA, cinnamate and salicylate. For example, octyl methoxycinnamate and 2-hydroxy-4- methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Adjunct optional ingredients in the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, Fullers earth, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these materials may range anywhere from 0.001% up to 20% by weight of the composition.

Furthermore, it is important to ensure that other ingredients do not interfere with the location of the crystals, e.g. if a high HLB emulsifier is used, it may destroy the crystals.

Making the Composition

The preferred method of preparing the inventive compositions includes the following steps:

(1) preparing an aqueous phase and heating to 75°–80° C., while mixing;

(2) preparing an oil phase, containing a fluid oil and a barrier ingredient components, but not a retinoid, and heating to 75°–80° C. while mixing;

(3) adding slowly the oil phase to the aqueous phase, with both phases at 75°–80° C.;

(4) mixing the mixture obtained in step (3) for at least 15 minutes at 75°–80° C.;

(5) adding a retinoid after cooling the mixture to 50°–55° C., while mixing;

(6) filling in storage containers.

If the final composition contains a hydroxyacid, it is preferably added separately, after step (4), at 50°–60° C.

Use of the Composition

The composition according to the invention is intended primarily as a product for topical application to human skin, especially as an agent for conditioning and smoothening the skin, and preventing or reducing the appearance of wrinkled or aged skin. In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

Product Form and Packaging

The inventive emulsions can be formulated as a lotion, a fluid cream, a cream, or a gel. The composition can be packaged in a suitable container to suit its viscosity and intended use by the consumer. For example, a lotion or fluid cream can be packaged in a bottle or a roll-ball applicator, or a capsule, or a propellant-driven aerosol device or a container fitted with a pump suitable for finger operation. When the composition is a cream, it can simply be stored in a non-deformable bottle or squeeze container, such as a tube or a lidded jar.

The invention accordingly also provides a closed container containing a cosmetically acceptable composition as herein defined.

The following specific examples further illustrate the invention, but the invention is not limited thereto.

Stability Evaluation:

A composition to be tested is prepared and packaged in a jar or in an HDPE tube. The jar or the tube is sealed and placed for storage in an oven at 30° C., 41° C. or 50° C. The stability study conducted at 50° C. is an accelerated stability study. Half-lifetimes depend on temperature in the ration 1:6:9:18 for 50° C.:30° C.:25° C.:20° C. For example, a half-lifetime of 40 days at 50° C. corresponds to 8 months at 30° C., 1 year at 25° C. (standard room temperature), and 2 years at 20° C. Furthermore, stability study was accelerated by storing samples in unfavorable conditions in the presence of an excess oxygen as described below. For optimum stability in commercial samples we recommend to place the system in an inert atmosphere of argon (pref.) or nitrogen, the absence of excess air will increase retinol stability by at least a factor of two. For stability studies done under aerated conditions, the tube or the jar is filled ⅓ with a composition and ⅔ head space and aerated at each time point. The composition is analyzed at regular time intervals until less than 10% of initial retinol is left unooxidized.

All stability studies in the Examples below were done under aerated conditions.

Our studies have shown that retinol oxidation in compositions evaluated for this invention follows a first order kinetic with respect to retinol concentration. Hence to determine the reaction half-lifetime one would plot the natural logarithm of the retinol concentration (lnC) against the storage time (t) and get a straight line with a slope −k where k is the rate of retinol oxidation in reciprocal unit of time. The half-life of retinol (t½) in the system under study is then determined by the ratio ln2/k.

Analysis of Retinol by HPLC

All samples care analyzed for retinol content using high pressure liquid chromatography (hardware: Waters 600-MS system controller, Waters 717 autosampler, Waters 996 photodiode array detector, software: Millenium 2010). Column parameters used for retinol analysis are as follows:

| Column: | Nucleosil C18 5 μm (Sigma-Aldrich) 250 mm × 4.6 mm |
|---|---|
| Catalog #: | Z226181 |
| Mobile Phase: | 47% (v/v) Acetonitrile 45% (v/v) Methanol 8% (v/v) Methylene Chloride All HPLC Grade Solvents. |
| Injection volume: | 10 μl |
| Flow Rate: | 1 ml/min |
| Run Time: | 10 minutes |
| Detector: | UV/VISIBLE at 325 nm with Photodiode Array |
| Retention Time: | ca. 5 minutes for retinol. |

Standard Solutions Preparation

A standard curve is generated whenever samples are analyzed for retinol content. Retinol standard solutions are prepared by diluting serially the retinol blend in isopropanol to yield standard solutions with final concentrations of 0, 10, 20, 30, 40, and 50 ppm (w/w). Standard solutions are prepared on a weekly basis and are stored at −21° C.

9

Sample Preparation

Most samples are prepared by simple dilution in isopropanol so that final retinol concentrations is within the range of the standard curve, preferentially around 30 ppm.

Emulsion samples such as thick creams containing gums are more difficult to prepare. In order to ensure the complete extraction of retinol from the emulsion, the sample is treated in the following manner: About 0.5 g of sample, measured precisely, is initially mixed with 6 to 7 grams of water and vortexed to form a slurry. Approximately 10 grams of isopropanol is then added to the slurry followed by a second vortexing period. The sample is then brought to final weight with isopropanol. The sample is subsequently filtered using a disposable syringe fitted with a 0.2 µm disposable filter.

All samples are prepared in triplicate or quintuplicate on a w/w basis using an analytical balance.

Analysis of Retinyl Acetate by HPLC

Use the same method and same mobile phase as with retinol. Retinyl acetate elutes about 30 sec. after retinol.

EXAMPLE 1

Compositions 1, 2, and 3 (all within the scope of the invention) were prepared.

10

The following procedure was employed to make the compositions:
1. Heat water phase (A) to 75°–80° C. while mixing in overhead mixer.
2. Heat oil phase (B) to 75°–80° C. while mixing
3. Slowly add oil phase (B) to water phase (A) with both phases at 75°–80° C.
4. Use water from (C) heated to 75°–80° C. to flush remainder of oil phase
5. Mix for at least 15 min. at 75°–80° C.
6. Begin cooling
7. Prepare phase (D) at room temperature and add to (ABC) at 50°–60° C.
8. Add retinol blend (E) to batch at 50° C.–55° C. while mixing
9. Mix while cooling to 40° C.
10. Add (F) at 40° C. while mixing
11. Stop mixing and fill in storage containers Observations:

Compositions 1, 2, and 3 essentially had similar characteristics when observed under a light microscope: spherical oil droplets about 50 microns in diameter, surrounded by a crystalline barrier layer as determined by the existence of a bright birefringent circle at the perimeter of each droplet

| PHASE | CHEMICAL/ CTFA NAME | TRADE NAME | COMP. 1 (WT. %) | COMP. 2 (WT. %) | COMP. 3 (WT. %) |
|---|---|---|---|---|---|
| A | WATER, DI | | 44.0 | 44.0 | 44.0 |
| A | DISODIUM EDTA | SEQUESTERENE Na2 | 0.05 | 0.05 | 0.05 |
| A | MAGNESIUM ALUMINUM SILICATE | VEEGUM ULTRA | 0.6 | 0.6 | 0.6 |
| A | METHYL PARABEN | METHYL PARABEN | 0.15 | 0.15 | 0.15 |
| A | SIMETHICONE | ANTIFOAM EMULSION | 0.01 | 0.01 | 0.01 |
| A | BUTYLENE GLYCOL - 1,3 | BUTYLENE GLYCOL - 1,3 | 3.0 | 3.0 | 3.0 |
| A | HYDROXYETHYLECELLULOSE | NATROSOL 250 HHR | 0.5 | 0.5 | 0.5 |
| A | GLYCERIN USP | GLYCERIN USP | 2.0 | 2.0 | 2.0 |
| A | XANTHAN GUM | KELTROL M | 0.2 | 0.2 | 0.2 |
| A | TRIETHANOLAMINE 99% | TEA 99% | 1.2 | 1.2 | 1.2 |
| B | STEARIC ACID[1] | PRISTERENE 4911 | 3.0 | 3.0 | 3.0 |
| B | GLYCERYL HYDROXYSTEARATE[1] | NATURECHEM GMHS | 1.5 | 1.5 | 1.5 |
| B | STEARYL ALCOHOL[1] | LANETTE 18DEO | 1.5 | 1.5 | 1.5 |
| B | CHOLESTEROL NF[1] | CHOLESTROL NF | 0.5 | 0.5 | 0.5 |
| B | SORBITAN STEARATE | SORBITAN STEARATE | 1.0 | 1.0 | 1.0 |
| B | PEG-100 STEARATE | MYRJ 59 | 2.0 | 2.0 | 2.0 |
| B | ISOSTEARYL PALMITATE[2] | PROTACHEM ISP | 6.0 | B.0 | 6.0 |
| B | C12–C15 ALCOHOLS OCTANOATE[2] | HESTESTER FAO | 3.0 | 3.0 | 3.0 |
| B | DIMETHICONE[2] | SILICONE FLD 200 (50 CTS) | 1.0 | 1.0 | 1.0 |
| B | TOCOPHERYL ACETATE | VITAMIN E ACETATE | 0.1 | 0.1 | 0.1 |
| B | BUTYLATED HYDROXYTOLUENE | BHT | 0.05 | 0.05 | 0.05 |
| B | PROPYLPARABEN NF | PROPYLPARABEN NF | 0.1 | 0.1 | 0.1 |
| C | WATER, DI | | 3.0 | 3.0 | 3.0 |
| D | L-LACTIC ACID (88%) | | — | — | 9.1 |
| D | GLYCOLIC ACID 70% | GLYPURE 70 | 11.4 | — | — |
| D | AMMONIUM HYDROXIDE 29% | AMMONIUM HYDROX. 29% | 2.5 | — | 2.5 |
| D | WATER, DI | | 99.51 | 99.51 | 99.51 |
| A | WATER, DI | | 44.0 | 44.0 | 44.0 |
| E | RETINOL (51.3%)[3] | RETINOL BLEND (51.3%) | 0.29 | 0.29 | 0.29 |
| F | ALPHA-BISABOLOL | ALPHA-BISABOLOL | 0.2 | 0.2 | 0.2 |
| | pH | | 3.6 | 7.0 | 3.9 |

[1]Barrier ingredients: glyceryl hydroxystearate is a crystal-sizing compound, the rest are crystal forming.
[2]Fluid oil
[3]A blend containing retinol - 51.3%, BHA - 0.6%, BHT - 3.1% and Tween 20 - 45%. (This blend was used in all the Examples herein)

when observed under cross-polar. This was confirmed by the fact that the bulk aqueous phase was essentially free of individual crystals. Using the Microscopic Crystal Sizing Test, crystals were found to be regular shaped and about 8 microns in diameter.

COMPARATIVE EXAMPLE 2

COMPARATIVE COMPOSITIONS A, B, C, D, E, F and G (all outside the scope of the invention) were prepared:

| INGREDIENT | (WT %) | | | | | | |
|---|---|---|---|---|---|---|---|
| | A | B | C | D | E | F | G |
| RETINOL BLEND | 0.29 | 0.29 | 0.99 | 0.99 | 0.99 | 0.99 | 0.99 |
| LIGHT MINERAL OIL | 99.71 | — | — | — | — | — | 99.01 |
| DISODIUM EDTA | — | 0.1 | — | — | — | — | — |
| WATER | — | 99.61 | — | — | — | — | — |
| TWEEN 20 | — | — | 99.01 | — | — | — | — |
| BUTYLENE GLYCOL | — | — | — | 99.01 | — | — | — |
| GLYCERINE | — | — | — | — | 99.01 | — | — |
| DECYL ALCOHOL | — | — | — | — | — | 99.01 | — |

Retinol blend was either totally soluble or readily dispersible in A through G. Compositions A through G did not contain barrier ingredients.

The storage stability of compositions 1–3 and comparative compositions A through G was measured according to the procedure described above (aerated test was employed). The results that were obtained are summarized in Tables 1, 1A, and 1B.

TABLE 1

STORAGE STABILITY

RETINOL CONCENTRATION (% OF INITIAL)

| TIME (DAYS) | COMPOSITION 1 | | COMPOSITION 2 | | COMPOSITION 3 | |
|---|---|---|---|---|---|---|
| | 30° C. | 50° C. | 30° C. | 50° C. | 30° C. | 50° C. |
| 0 | 100 | 100 | 100 | 100 | 100 | 100 |
| 9 | 96 | 54 | 94 | 89 | 89 | 45 |
| 16 | | 45 | 98 | 82 | 98 | 38 |
| 22 | 94 | 35 | 97 | 71 | 96 | 24 |
| 31 | 89 | 22 | 95 | 60 | 92 | 20 |
| 63 | 75 | — | 88 | 32 | 81 | — |
| 84 | 65 | — | 80 | — | 72 | — |
| 126 | 50 | 1 | 71 | 11 | 60 | 1 |
| 196 | 33 | — | 60 | 0 | 39 | — |
| Half-life (Days) | 120 | 20 | 260 | 39 | 149 | 20 |

TABLE 1A

STORAGE STABILITY

RETINOL CONCENTRATION (% OF INITIAL)

| TIME (DAYS) | COMP. A | | | COMP. B | | |
|---|---|---|---|---|---|---|
| | 30° C. | 43° C. | 50° C. | 30° C. | 43° C. | 50° C. |
| 0 | 100 | 100 | 100 | 100 | 100 | 100 |
| 8 | 101 | 98 | 88 | | 55 | 10 |
| 10 | | | | 81 | 18 | 4 |
| 15 | 94 | 85 | 74 | 61 | 10 | 1 |
| 21 | 95 | 84 | 70 | 46 | 6 | 0.9 |
| 29 | 96 | 81 | 62 | 46 | | |
| 42 | 89 | 71 | 48 | 28 | | |
| 64 | 89 | 62 | 37 | 16 | | |
| 120 | 80 | 35 | 8 | | | |
| 168 | 67 | | | 0 | | |
| 238 | 57 | 15 | | | | |
| Half-life (Days) | 297 | | 34 | 24 | | 2 |

TABLE 1B

STORAGE STABILITY

| Time (hours) | Retinol Concentration (% of initial) Upon Storage at 90° C. | | | | |
|---|---|---|---|---|---|
| | Comp. C | Comp. D | Comp. E | Comp. F | Comp. G |
| 0 | 100 | 100 | 100 | 100 | 100 |
| 5 | 64 | 78 | 55 | 63 | 89 |
| 22 | | 4 | 37 | 29 | 69 |
| 29 | 30 | | 23 | | 67 |
| 48 | 35 | 3 | 16 | 19 | 63 |
| 72 | 21 | 3 | 6 | 11 | 49 |
| Half-Life (hours) | 36 | 14 | 19 | 25 | 77 |

Observations:

Storage stability measurements of compositions A and B (Table 1 A) show that retinol is much more stable in an oil environment (composition A) than in a water environment (composition B): t½ for A is 34 days at 50° C. (297 days at 30° C.) vs. 2 days at 50° C. (24 days at 30° C.) for B. Unexpectedly, compositions 1 through 3 exhibited a retinol stability similar to that of retinol in mineral oil (composition A): t½ for 1, 2, and 3 are 20, 39, and 20 days at 50° C., respectively, and 120, 260, 149 days at 30° C., respectively. The retinol stability of compositions 1 through 3 is remarkable considering the fact that these systems contain 80% w/w continuous aqueous phase. Retinol is stabilized because it is kept in a discrete oil microenvironment within the emulsion by the presence of the interfacial crystalline barrier of the invention.

Compositions C through G show that retinol is more unstable in a polar environment such as Tween 20, butylene glycol, glycerin, or decyl alcohol ( t½ is 36 hours, 14 hours, 19 hours, and 25 hours at 90° C. respectively) than in an a polar environment such as mineral oil (t½ is 77 hours at 90° C.). Since the more polar the environment, the less stable the retinoids we can understand why retinol or short chain retinol esters are less stable than long chain esters such as retinyl palmitate in emulsion systems. Retinol or short chain retinol esters are more polar than long chain esters such as retinyl palmitate, being more polar they will have the tendency to partition more favorably into polar solvents such as water than long chain esters. The more they partition away from the oil and into polar solvent the more unstable they are explaining why retinyl palmitate is generally more stable than retinol or retinyl acetate in emulsion systems (cf. B. Idson, C&T, Vol 108, p 86: "vitamin A palmitate is the most stable of available vitamin A esters", Roche: "retinol is more sensitive than fatty acid esters of vitamin A").

COMPARATIVE EXAMPLE 3

Compositions G and H (both outside the scope of the invention) were prepared. Both compositions contained retinol capsules, i.e. retinol in petroleum jelly dispersed in a hardened polyacrylic/carraghenan gel forming a capsule which was then further dispersed (cold) in a final composition (G or H). The resulting compositions were outside the scope of the invention.

| | Composition of retinol capsules: | |
|---|---|---|
| A | snow petrolatum | 17.1% |
| A | retinol blend | 3.1% |
| B | Aculyn 33 solution (4% neutralized to pH 7) | 45.3% |
| B | Gelcarin 6P-911 (kappa carraghenan) | 34.5% |

Capsules preparation: Mix retinol and snow petrolatum at 40°–45° C. to form phase A. Heat to 60°–70° C. an Aculyn 33 (polyacrylic acid) solution previously neutralized to pH 7 and add the carraghenan. Add B to A and emulsify for 4 minutes at 650 rpm using low shear homogenization (e.g., Denver flotation instrument). Make capsules by pouring the emulsion drop by drop in a hardening bath made of 10% KCL and 0.5% triton X-100. The capsules are then dried on a filter paper, weighed and added cold by gentle hand-stirring to a concentrate emulsion of the invention. The other components listed in Table 2 were added cold by gentle stirring. The retinol content in both compositions G and H was measured to be 0.1% at the start of the storage period.

TABLE 2

| | COMPOSITION | |
|---|---|---|
| INGREDIENT | PERCENT G | PERCENT H |
| Emulsion Base* Concentrate | 74.96 | 69.54 |
| Glycolic Acid 70% | 11.43 | 11.43 |
| HCA | 0.1 | — |
| NH₄OH (29%) | 2.5 | 8.7 |
| HCe | — | 0.1 |
| Retinol Capsules | 10 | 10 |
| Alpha Bisabolol | 0.2 | 0.2 |
| Fragrance | 0.03 | 0.03 |
| Water | ← to 100 → | |
| pH | 3.5 | 7.0 |

*Same composition as composition 1 in Example 1, except that phases D and E were not included.

Although compositions G and H contained the barrier ingredients as composition 1 in Example 1, those ingredients did not serve as a barrier layer around retinol, because retinol capsules were postadded to composition 1, to produce compositions G and H. Both compositions G and H contained retinol solubilized in a fluid oil phase, but this oil phase was not surrounded by a combination of barrier ingredients forming a crystalline barrier layer according to the invention. Fluorescence micrographs showed that retinol was localized within the petrolatum phase of the capsule. Light microscopy did not show the presence of a uniform interfacial barrier but showed the presence of randomly dispersed crystals within the petrolatum.

The storage stability of compositions G and H was measured according to the procedure described above (aerated test was employed). The results that were obtained are summarized in Table 3.

TABLE 3

| STORAGE STABILITY RETINOL CONCENTRATION (% OF INITIAL) | | | | |
|---|---|---|---|---|
| | COMPOSITION G | | COMPOSITION H | |
| TIME (DAYS) | 30° C. | 50° C. | 30° C. | 50° C. |
| 0 | 100 | 100 | 100 | 100 |
| 4 | — | 83 | — | 74 |
| 7 | — | 56 | — | 65 |
| 14 | 97 | 23 | 80 | 43 |
| 21 | — | 10 | — | 28 |
| 28 | 68 | 5 | 70 | 20 |
| 52 | 48 | — | 64 | — |
| 112 | 21 | — | 49 | — |
| Half-life (Days) | 48 | 6 | 120 | 12 |

The storage stability results in Table 4 were compared to the storage stability of compositions 4 and 5 in Table 2. By contrast with compositions G and H, compositions 4 and 5 contained barrier ingredients around retinol droplets.

In the absence of the barrier ingredients of the invention around retinol, the half-life decreased from 20 days for composition 1 to 6 days for composition G at 50° C.; and from 39 days for composition 2 to 12 days for composition H. This is evidence of the crucial role of the presence of barrier ingredients around retinol droplets in stabilizing retinoids in compositions of the invention.

This example also demonstrates the criticality of employing the inventive process in manufacturing the inventive compositions.

COMPARATIVE EXAMPLE 4

Composition K was prepared (outside the scope of the invention). The composition contained a crystal-sizing component in the barrier ingredient, but no crystal-forming ingredient. Composition K was identical to composition 1 (pH=3.6) except that crystal-forming ingredients, i.e. stearic acid and stearyl alcohol were absent from composition K.

The storage stability of composition K was measured according to the procedure described above (aerated test was employed). The results that were obtained are summarized in Table 4.

TABLE 4

| STORAGE STABILITY | | |
|---|---|---|
| | RETINOL CONCENTRATION (% OF INITIAL) | |
| TIME (DAYS) | 30° C. | 50° C. |
| 0 | 100 | 100 |
| 7 | N.D. | 30 |
| 14 | 73 | 10 |
| 21 | — | 4 |
| 28 | 54 | N.D. |
| Half-life (Days) | 31 | 4 |

The storage stability results in Table 4 were compared to the storage stability of compositions 1 and 2 in Example 1. In the absence of the crystal-forming ingredients of the invention, the half-life decreased from 20 days (composition 1) to 4 days (composition K) at 50° C. This is evidence of the crucial role of the crystal-forming ingredients in stabilizing retinoids in compositions of the invention. Microscopic observation of composition K revealed the presence of very small crystals, less than 1 micron in diameter (outside the range recited by the present claims).

COMPARATIVE EXAMPLE 5

Composition L was prepared (outside the scope of the invention). The composition contained a crystal-forming component in the barrier ingredient, but no crystal-sizing ingredient.

Retinol concentrate was prepared by adding B to A at 73° C. while mixing at 500 rpm for 15 minutes at 45°–55° C. Then the concentrate was added at 35°–40° C. to composition 1, except that phases D and E were absent, to yield a retinol concentration of about 0.1%. Alpha hydroxyacids were added to yield a pH=3.6.

| Retinol concentrate: | | |
|---|---|---|
| A | water DI | 59.25% |
| A | Keltrol 1000 | 0.5% |
| A | TEA (99%) | 0.25% |
| B | behenic acid | 12% |
| B | ISP | 20% |
| B | retinol blend | 8% |
| composition L: | | |
| modified composition 1 | | 74.96% |
| water DI | | 5% |
| glycolic acid (70%) | | 11.4% |
| ammonium hydroxide (29%) | | 2.5% |
| hydroxycaprylic acid | | 0.1% |
| retinol concentrate | | 3.3% |
| water DI | | 2.51% |
| bisabolol | | 0.2% |
| fragrance | | 0.03% |

Storage stability was measured. The results that were obtained are summarized in Table 5.

TABLE 5

| | STORAGE STABILITY | |
|---|---|---|
| | RETINOL CONCENTRATION (% OF INITIAL) | |
| TIME (DAYS) | 30° C. | 50° C. |
| 0 | 100 | 100 |
| 7 | — | 28 |
| 14 | 79 | 28 |
| 21 | 66 | 11 |
| 35 | 62 | 4 |
| 42 | 55 | — |
| 59 | 43 | — |
| 71 | 39 | — |
| T ½ (DAYS) | 53 | 8 |

In the absence of the crystal sizing ingredients of the invention, the half-life decreased from 20 days to 8 days at 50° C. in compositions 1 and L, respectively. This is evidence of the crucial role of the crystal sizing ingredients in stabilizing retinoids in compositions of the invention.

The lack of crystal sizing ingredients manifested itself by the presence of large irregularly-sized crystals (about 60 microns in diameter) when observed under the microscope.

COMPARATIVE EXAMPLE 6

Composition M and N were prepared (outside the scope of the invention). The compositions contained a fluid oil incompatible with retinol (a high molecular weight silicone oil).

First, a concentrate retinol dispersion in the incompatible oil (high molecular weight silicone oil from Dow) was prepared. Then the concentrate was added at 50°–55° C. to composition 1 except that phases D and E were absent to yield a retinol concentration of about 0.05%.

| Retinol Concentrate Dispersion: | |
|---|---|
| Dow 200 10,000 cst fluid | 79.4% |
| cab o sil TS 720 | 9% |
| retinol blend (Roche) | 11.6% |
| Composition M | |
| modified composition 1 | 74.96% |
| water DI | 16.8% |
| retinol concentrate dispersion | 8% |
| bisabolol | 0.2% |
| fragrance | 0.03% |
| pH | 7.4 |
| Composition N | |
| modified composition 1 | 74.96% |
| water DI | 2.81% |
| glycolic acid (70%) | 11.4 |
| ammonium hydroxide (29%) | 2.5% |
| hydroxycaprylic acid | 0.1% |
| retinol concentrate dispersion | 8% |
| bisabolol | 0.2% |
| fragrance | 0.03% |
| pH | 3.7 |

Storage stability of compositions M and N was measured. The results that were obtained are summarized in Table 6.

TABLE 6

| | STORAGE STABILITY RETINOL CONCENTRATION (% OF INITIAL) | | | |
|---|---|---|---|---|
| | M | | N | |
| TIME (DAYS) | 30° C. | 50° C. | 30° C. | 50° C. |
| 0 | 100 | 100 | 100 | 100 |
| 7 | — | 58 | — | 25 |
| 17 | 55 | 30 | 23 | 6 |
| 24 | — | 18 | — | — |
| 29 | 50 | 20 | 17 | — |
| 36 | — | 13 | — | — |
| 42 | 43 | — | 11 | — |
| 55 | 28 | 5 | — | — |
| T ½ (DAYS) | 13 | 4 | 33 | 13 |

In the absence of a retinoid compatible oil of the invention, the half-life decreased from 20 days to 4 days at 50° C. in compositions 1 and N, respectively, and from 39 days to 13 days in compositions 2 and M, respectively. Retinoids were kept from diffusing into the oil phase of the invention by using silica to trap the retinoids into the silicone droplets where they were insoluble as evidenced by observation under light microscope (retinol disperses as distinct droplet in high molecular weight silicone but does not solubilize). This is evidence of the crucial role of the fluid oil in stabilizing retinoids in compositions of the invention.

EXAMPLE 7

Objective

The objective of this study was to evaluate the efficacy of the following formulations:

1. 8% L-Lactic vs 8% L-Lactic/0.174% Retinyl Acetate (both in emulsion base)
2. 8% L-Lactic vs 8% L-Lactic/0.25% Retinyl Palmitate (both in emulsion base)
3. 8% L-Lactic/0.075% Retinol vs 8% L-Lactic/0.09% Retinyl Acetate (both in emulsion base)

Treatment group 1 contained 16 female subjects (aged 45 or older) whereas groups 2 and 3 contained 17 subjects each.

These formulations are not within the scope of the invention: the study was conducted merely to establish a relative efficacy of retinol vs. retinyl acetate vs. retinyl palmitate, not to evaluate the stability.

EMULSION BASE

| CHEMICAL/CFTA NAME | TRADE NAME | LEVEL % |
|---|---|---|
| Triethanolamine | TEA 99% | 5.0 |
| Butylene glycol | Butylene glycol | 3.0 |
| Xanthan gum | Keltrol 1000 | 1.0 |
| Disodium EDTA | Hampene Na2 | 0.1 |
| Methyl- and propyl-paraben, and diazolidinyl urea, and propylene glycol | Germaben IIE | 1.0 |
| BHA | Embanox BHA | 0.005 |
| BHT | Nipanox BHT | 0.005 |
| Octylmethoxycinnamate | Neoheliopan AV | 3.0 |
| Caprylic/capric triglyceride | Miglyol 812 | 3.6 |
| Polysorbate 20 | Tween 20 | 0.4 |
| 0.5% D&C yellow | | 0.4 |
| DI water | | to 100% |

Within each treatment group, test products were left/right randomized. Subjects self administered the test products at home, twice daily (morning and evening) for twelve weeks. The test was conducted double-blind. Fifty female subjects with moderate crepiness on the lower arm participated. Subjects continued their normal cleansing routine, but were instructed that they must not apply any moisturizing products to their forearms and hands for one week prior to the baseline visit (Week 0). At baseline, Weeks 2, 4, 8 and 12, a visual evaluation (evaluation included assessment of a crepe-like condition and overall appearance) was conducted. Whenever possible, the evaluations were conducted in the same location under consistent lighting. All products were weighed at each visit to determine usage compliance.

Assessment: Clinical Evaluation

The following parameters were evaluated by a trained assessor.

Outer Forearms:

crepe-like/crinkled skin—loose/surface saggy/lined/wrinkled skin can improvement indicates firmer, less lined/wrinkled)

overall appearance (photodamage)—a global assessment of the condition of the area with respect to texture and overall surface features (an improvement indicates better overall skin condition)

0 to 9 point evaluation scale of crepe-like/crinkled skin was used:

MILD 1–3

Small, circular fine lines May not be real obvious at first glance; see more with twisting of the skin Less than 25% of the lower outer forearm/back of hand

MODERATE 4–6

Obvious lined pattern, circular lines with "puffy" look More than 25% coverage but not entire outer lower arm/back of hand

SEVERE 7–9

Up to 100% coverage of the outer lower forearm/back of hand Very obvious, well demarcated Long "puffy" (depth) longitudinal lines Mid-category grades were assigned for responses not warranting a full category increase.

Neither the assessor nor the study subject were aware of the identity of the formulations tested.

STATISTICAL ANALYSIS

Raw data was analyzed using a SAS-based macro computer program %WSIGNRNK, which performs the Wilcoxon Signed-Rank, Pfaff version.

Statistical analyses were performed separately for each matched-pair product comparison, test site (outer forearm, back of hand), evaluation time point and attribute measure. A paired comparison statistical analyses were performed for each treatment group. The differences were judged to be statistically significant at $p > 95\%$.

Clinical assessment of differences between treatment comparisons is summarized in Tables 7A–7C below.

TABLE 7A

8% L-lactic acid (8LL) vs 0.174% Retinyl Acetate (RA)
Positive crepe scale differences favor RA

| | 9-point Crepe scale | | |
|---|---|---|---|
| week | 8LL | RA | Difference |
| 0 | 4.2813 | 4.2813 | 0 |
| 2 | 4.2667 | 4.2333 | 0.0333 |
| 4 | 4.4333 | 4.4000 | 0.0333 |
| 8 | 4.1667 | 3.9333 | 0.2333* |
| 12 | 3.9000 | 3.7667 | 0.13333 |

*statistically significant

TABLE 7B

8% L-lactic acid (8LL) vs 8% L-lactic acid + 0.25% Retinyl Palmitate (8LLRP)
Positive crepe scale differences favor 8LLRP

| | 9-point Crepe scale | | |
|---|---|---|---|
| week | 8LL | 8LLRP | Difference |
| 0 | 4.4118 | 4.4118 | 0 |
| 2 | 4.3235 | 4.3529 | –0.0294 |
| 4 | 4.5000 | 4.4118 | 0.0882 |
| 8 | 4.2647 | 4.2353 | 0.0294 |
| 12 | 4.0313 | 4.0625 | –0.0313 |

TABLE 7C

8% L-lactic acid + 0.075% Retinol (8LLR) vs
8% L-lactic acid + 0.09% Retinyl Acetate (8LLRA)
Positive crepe scale differences favor 8LLRA

| | 9-point Crepe scale | | |
|---|---|---|---|
| week | 8LLR | 8LLRA | Difference |
| 0 | 4.7353 | 4.7353 | 0 |
| 2 | 4.6875 | 4.7188 | –0.0313 |
| 4 | 4.5588 | 4.6765 | –0.1176 |
| 8 | 4.2941 | 4.2353 | 0.0588 |
| 12 | 3.8667 | 4.2333 | –0.3667* |

*statistically significant

Results: A composition containing 8% L-lactic acid and 0.25% retinyl palmitate did not yield significantly more improvement to crepe-like arm skin than 8% L-lactic acid in the same base formulation. In contrast, the same base formulation containing 8% L-lactic acid and 0.17% retinyl acetate yielded significantly more clinically determined improvement to crepe-like skin by both clinician rating and forced choice (the latter results not shown here) over 8% L-lactic acid in the same base formulation (p>95% at week 8). Moreover, the same base formulation containing 8% L-lactic acid and 0.075% retinol yielded significantly more clinically determined improvement to crepe-like skin by both clinician rating and forced choice over 8% L-lactic acid and 0.09% retinyl acetate in the same base formulation (p>95% at week 12).

In conclusion, retinyl palmitate did not increase the anti-aging efficacy of a hydroxy acid formulation while retinyl acetate did. The efficacy was further improved when retinol was used instead of retinyl acetate making retinol the most preferred retinoid to be used in the present invention.

EXAMPLE 8

The following additional compositions within the scope of the invention were prepared.

| | | COMPOSITION | | |
|---|---|---|---|---|
| Ingredient | Chemical/CTFA Name | 8A wt/wt % | 8B wt/wt % | 8C wt/wt % |
| Water DI | Same | 47.10 | 47.28 | 51.41 |
| Disodium EDTA | Same | 0.05 | 0.05 | 0.05 |
| Veegum Ultra | Magnesium Aluminum Silicate | 0.60 | 0.60 | 0.60 |
| Methyl Paraben | Same | 0.15 | 0.15 | 0.15 |
| Aloe Vera Powder | Aloe Vera Gel | 0.10 | 0.10 | 0.10 |
| Triethanolamine (99%) | Same | 1.20 | 1.20 | 1.20 |
| Antifoam | Simethicone | 0.01 | 0.01 | 0.01 |
| Glycerin | Same | 2.00 | 2.00 | 2.00 |
| Butylene Glycol | Same | 3.00 | 3.00 | 3.00 |
| Keltrol CG1000 | Xanthan Gum | 0.20 | 0.20 | 0.20 |
| Natrosol 250HHR | Hydroxyethylcellulose | 0.30 | 0.30 | 0.50 |
| Water DI Flush | Same | 1.00 | 1.00 | 1.00 |
| Pationic SSL | Sodium Stearyl Lactylate | | | 0.50 |
| Naturchem GMHS | Glyceryl Hydroxystearate | 1.50 | 1.50 | 1.50 |
| Lanette 18 DEO | Stearyl Alcohol | 1.50 | 1.50 | 1.50 |
| Parsol MCX | Octyl Methoxycinnamate Ethylhexyl P-Methoxycinnamate | 7.50 | 7.50 | |
| Uvinol M-40 | Benzophenone-3 Oxybenzone | 2.50 | 2.50 | |
| Finsolv TN | C12–15 Alkyl Benzoate | 3.00 | 3.00 | |
| Protachem ISP | Isostearyl Palmitate | | | 6.00 |
| Hetester FAO/Fine | C12–15 Alkyl Octanate | | | 3.00 |
| Silicone Fluid 50 | Dimethicone | | | 1.00 |
| Cholesterol | Same | 0.50 | 0.50 | 0.50 |
| Arlacel 60 | Sorbitan Stearate | 1.00 | 1.00 | 1.00 |
| BHT | Butylated Hydroxytoluene | 0.05 | 0.05 | 0.05 |
| Vitamin E Acetate | Tocopheryl Acetate | 0.10 | 0.10 | 0.10 |
| Myrj 59 | PEG-100 Stearate | 2.00 | 2.00 | 2.00 |
| Pristerene 4911 | Stearic Acid | 3.00 | 3.00 | 3.00 |
| Propylparaben | Same | 0.10 | 0.10 | 0.10 |
| Silicone Fluid 10 | Dimethicone | 2.00 | 2.00 | |
| Linoleamide MEA | Same | 1.00 | 1.00 | |
| Water DI Flush | Same | 1.50 | 1.50 | 1.47 |
| Water DI | Same | 8.00 | 8.00 | 8.29 |
| Hydroxycaprylic Acid | Same | | | 0.10 |
| Glycolic Acid 70% | Same | 5.70 | 5.70 | 5.70 |
| Ammonia, Aqua 28% | Ammonium Hydroxide | 1.30 | 1.30 | 1.20 |
| Water Di Flush | Same | 1.50 | 1.50 | 2.23 |
| Vitamin A Palmitate | Retinyl Palmitate | 0.10 | 0.10 | 0.10 |
| Bisabolol | Same | 0.20 | 0.20 | 0.20 |
| Fragrance | Same | 0.03 | 0.03 | 0.03 |
| Petinol 50% | Vitamin A Alcohol | 0.20 | 0.02 | 0.20 |
| Retinyl Acetate | Vitamin A Acetate | 0.01 | 0.01 | |
| | Total | 100.00 | 100.00 | 100.00 |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed:

1. A stable oil-in-water emulsion for a skin conditioning composition, the emulsion comprising:

(a) an oil phase comprising from about 0.1% to about 50%, by weight of the emulsion, of oil droplets comprising a fluid oil and from about 0.01% to about 10% by weight of the emulsion of a retinoid selected from the group consisting of retinol, retinyl acetate, and retinyl propionate, wherein the retinoid is solubilized in the oil; and wherein the fluid oil is selected from the group consisting of isostearyl palmitate, tridecyl salicylate, $C_{12-15}$ octaneate, isopropyl stearate, isopropyl myristate and isopropyl palmitate (b) from about 50% to about 98% of an aqueous phase containing at least 40% water; and (c) from about 1% to about 20% by weight of the emulsion of a barrier ingredient which comprises a crystal-forming compound and a crystal-sizing compound, wherein the barrier ingredient provides a crystalline barrier layer between the oil droplets and the aqueous phase, wherein the crystal-forming compound is selected from the group consisting of $C_{12}$–$C_{22}$ fatty acids, mixtures of $C_{12}$–$C_{22}$ fatty acids with their soaps, $C_{12}$–$C_{22}$ fatty alcohols, and mixtures thereof;

wherein the crystal-sizing compound is selected from the group consisting of hydroxylated $C_{12}$–$C_{22}$ fatty acids, hydroxylated fatty $C_{12}$–$C_{22}$ alcohols, and mixtures thereof; and wherein the average size of an individual crystal in the barrier layer, as determined by a Microscopic Crystal Sizing Test, is in the range of from about 1 µM to about 50 µm;

and wherein the size ratio of an individual oil droplet to an individual crystal in the barrier layer is in the range of from about 5:1 to about 100:1;

and wherein the melting point of a mixture of the fluid oil and the barrier ingredient is in the range of from about 40° C. to about 100° C.

2. The composition of claim 1, wherein the retinoid is selected from the group consisting of retinol and retinyl acetate.

3. The composition of claim 1 wherein the composition is essentially free of an alcohol selected from the group consisting of ethanol, methanol, propanol, and isopropanol.

4. The composition of claim 1 wherein the aqueous phase of the composition comprises an alpha hydroxy acid.

5. The composition of claim 4 wherein the amount of the alpha hydroxy acid is in the range from about 0.05% to about 12%.

6. The composition of claim 1 wherein the half-lifetime of the composition at 50° C. is at least 15 days.

7. A method of making a stable oil in water emulsion according to claim 1, the method comprising:

(1) preparing an aqueous phase and heating at temperature in the range of from about 75° C. to about 80° C., while mixing;

(2) preparing a mixture containing a fluid oil and barrier ingredient components and heating the mixture to a temperature in the range of from about 75° C. to about 80° C. while mixing;

(3) adding slowly the mixture of step (2) to the aqueous phase;

(4) mixing the mixture obtained in step (3) for at least 15 minutes at a temperature in the range of from about 75° C. to about 80° C.;

(5) adding a retinoid after cooling the mixture obtained in step (4) to a temperature in the range of from about 50° C. to about 55° C., while mixing;

(6) filling in storage containers.

8. The method of claim 7, further comprising adding a hydroxy acid, after step 4, at a temperature in the range of from about 50° C. to about 60° C.

* * * * *